US008636730B2

(12) United States Patent
Keppel (10) Patent No.: US 8,636,730 B2
(45) Date of Patent: Jan. 28, 2014

(54) POLARITY CONTROL OF ELECTROSURGICAL GENERATOR

(75) Inventor: David S. Keppel, Longmont, CO (US)

(73) Assignee: Covidien LP, Mansfield, MA (US)

( * ) Notice: Subject to any disclaimer, the term of this patent is extended or adjusted under 35 U.S.C. 154(b) by 371 days.

(21) Appl. No.: 12/834,364

(22) Filed: Jul. 12, 2010

(65) Prior Publication Data
US 2012/0010610 A1    Jan. 12, 2012

(51) Int. Cl.
*A61B 18/14* (2006.01)

(52) U.S. Cl.
USPC ............... 606/34; 606/38; 606/39; 606/40; 606/41

(58) Field of Classification Search
USPC ................. 606/30–50; 323/302, 911
See application file for complete search history.

(56) References Cited

U.S. PATENT DOCUMENTS

| | | | |
|---|---|---|---|
| 3,923,063 A | 12/1975 | Andrews et al. | |
| 3,952,748 A | 4/1976 | Kaliher et al. | |
| 3,963,030 A | 6/1976 | Newton | |
| 4,024,467 A | 5/1977 | Andrews et al. | |
| 4,188,927 A | 2/1980 | Harris | |
| 4,271,837 A * | 6/1981 | Schuler | 606/39 |
| 4,378,801 A | 4/1983 | Oosten | |
| 4,429,694 A | 2/1984 | McGreevy | |
| 4,438,766 A | 3/1984 | Bowers | |
| 4,520,818 A | 6/1985 | Mickiewicz | |
| 4,559,943 A | 12/1985 | Bowers | |
| 4,590,934 A | 5/1986 | Malis et al. | |
| 4,818,954 A * | 4/1989 | Flachenecker et al. | 331/183 |
| RE34,432 E | 11/1993 | Bertrand | |
| 5,370,645 A | 12/1994 | Klicek et al. | |
| 5,372,596 A | 12/1994 | Klicek et al. | |
| 5,451,224 A | 9/1995 | Goble et al. | |
| 5,472,443 A | 12/1995 | Cordis et al. | |
| 5,479,871 A | 1/1996 | Fox et al. | |
| 5,827,271 A | 10/1998 | Buysse et al. | |
| 5,836,943 A | 11/1998 | Miller, III | |
| 5,843,019 A | 12/1998 | Eggers et al. | |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

U.S. Appl. No. 10/406,690, Apr. 2003, Michael S. Klicek.*

(Continued)

*Primary Examiner* — Michael Peffley
*Assistant Examiner* — Khadijeh Vahdat (57) ABSTRACT

A method for controlling an electrosurgical generator is contemplated by the present disclosure. The method includes applying an electrosurgical waveform to tissue through an electrode. The electrosurgical waveform includes one or more positive half-cycles one or more negative half-cycles. The method also includes measuring voltage and current of the electrosurgical waveform to detect a peak voltage of each of the positive half-cycles and the negative half-cycles and comparing the peak voltage of the positive half-cycles and the peak voltage of the negative half-cycles to determine generation of electrical discharges. The method further includes adjusting the current of the electrosurgical waveform to regulate the generation of the electrical discharges based on a comparison of the peak voltage of the positive half-cycles and the peak voltage of the negative half-cycles.

20 Claims, 6 Drawing Sheets

(56) References Cited

U.S. PATENT DOCUMENTS

| | | | | |
|---|---|---|---|---|
| 5,849,010 | A | 12/1998 | Wurzer et al. | |
| 5,891,142 | A | 4/1999 | Eggers et al. | |
| 5,908,444 | A | 6/1999 | Azure | |
| 5,954,717 | A | 9/1999 | Behl et al. | |
| 5,971,980 | A | 10/1999 | Sherman | |
| 6,010,499 | A | 1/2000 | Cobb | |
| 6,039,732 | A | 3/2000 | Ichikawa et al. | |
| 6,056,746 | A | 5/2000 | Goble et al. | |
| 6,074,386 | A | 6/2000 | Goble et al. | |
| 6,093,186 | A | 7/2000 | Goble | |
| 6,142,992 | A | 11/2000 | Cheng et al. | |
| 6,186,147 | B1 | 2/2001 | Cobb | |
| 6,228,081 | B1 | 5/2001 | Goble | |
| 6,235,020 | B1 | 5/2001 | Cheng et al. | |
| 6,238,387 | B1 | 5/2001 | Miller, III | |
| 6,261,286 | B1 | 7/2001 | Goble et al. | |
| 6,293,942 | B1 | 9/2001 | Goble et al. | |
| 6,296,636 | B1 | 10/2001 | Cheng et al. | |
| 6,306,134 | B1 | 10/2001 | Goble et al. | |
| 6,364,877 | B1 | 4/2002 | Goble et al. | |
| 6,398,779 | B1 | 6/2002 | Buysse et al. | |
| 6,398,781 | B1 | 6/2002 | Goble et al. | |
| 6,413,256 | B1 | 7/2002 | Truckai et al. | |
| 6,416,509 | B1 | 7/2002 | Goble et al. | |
| 6,428,537 | B1 | 8/2002 | Swanson et al. | |
| 6,468,270 | B1 | 10/2002 | Hovda et al. | |
| 6,547,786 | B1 | 4/2003 | Goble | |
| 6,582,427 | B1* | 6/2003 | Goble et al. | 606/37 |
| 6,632,193 | B1 | 10/2003 | Davison et al. | |
| 6,692,489 | B1 | 2/2004 | Heim et al. | |
| 6,723,091 | B2 | 4/2004 | Goble et al. | |
| 6,784,405 | B2 | 8/2004 | Flugstad et al. | |
| 6,796,981 | B2 | 9/2004 | Wham et al. | |
| 6,837,888 | B2 | 1/2005 | Ciarrocca et al. | |
| 6,843,789 | B2 | 1/2005 | Goble | |
| 6,893,435 | B2 | 5/2005 | Goble | |
| 6,939,347 | B2 | 9/2005 | Thompson | |
| 6,942,660 | B2 | 9/2005 | Pantera et al. | |
| 6,974,453 | B2 | 12/2005 | Woloszko et al. | |
| 7,066,933 | B2 | 6/2006 | Hagg | |
| RE39,358 | E | 10/2006 | Goble | |
| 7,175,621 | B2 | 2/2007 | Heim et al. | |
| 7,195,627 | B2 | 3/2007 | Amoah et al. | |
| 7,211,081 | B2 | 5/2007 | Goble | |
| 7,220,260 | B2 | 5/2007 | Fleming et al. | |
| 7,255,694 | B2 | 8/2007 | Keppel | |
| 7,300,435 | B2 | 11/2007 | Wham et al. | |
| 7,303,557 | B2 | 12/2007 | Wham et al. | |
| 7,364,577 | B2 | 4/2008 | Wham et al. | |
| D574,323 | S | 8/2008 | Waaler | |
| 7,651,492 | B2 | 1/2010 | Wham | |
| 7,678,105 | B2 | 3/2010 | McGreevy et al. | |
| 7,956,620 | B2* | 6/2011 | Gilbert | 324/649 |
| 8,152,802 | B2* | 4/2012 | Podhajsky et al. | 606/34 |
| 8,162,932 | B2* | 4/2012 | Podhajsky et al. | 606/38 |
| 8,167,875 | B2* | 5/2012 | Podhajsky et al. | 606/34 |
| 8,211,100 | B2* | 7/2012 | Podhajsky et al. | 606/38 |
| 8,231,553 | B2* | 7/2012 | Joseph et al. | 600/590 |
| 8,235,917 | B2* | 8/2012 | Joseph et al. | 600/590 |
| 8,262,652 | B2* | 9/2012 | Podhajsky | 606/38 |
| 8,298,223 | B2* | 10/2012 | Wham et al. | 606/33 |
| 8,303,580 | B2* | 11/2012 | Wham et al. | 606/34 |
| 8,333,759 | B2* | 12/2012 | Podhajsky | 606/34 |
| 8,377,054 | B2* | 2/2013 | Gilbert | 606/34 |
| 8,382,751 | B2* | 2/2013 | Gilbert et al. | 606/38 |
| 8,454,590 | B2* | 6/2013 | Smith | 606/34 |
| 2002/0029036 | A1 | 3/2002 | Goble | |
| 2003/0181898 | A1 | 9/2003 | Bowers | |
| 2004/0167508 | A1* | 8/2004 | Wham et al. | 606/32 |
| 2005/0004634 | A1 | 1/2005 | Ricart | |
| 2006/0178664 | A1* | 8/2006 | Keppel | 606/34 |
| 2006/0219682 | A1 | 10/2006 | Klett et al. | |
| 2007/0250052 | A1 | 10/2007 | Wham | |
| 2007/0282320 | A1 | 12/2007 | Buysse et al. | |
| 2008/0082095 | A1 | 4/2008 | Shores et al. | |
| 2009/0048595 | A1 | 2/2009 | Mihori | |
| 2009/0082765 | A1 | 3/2009 | Collins | |
| 2009/0254077 | A1 | 10/2009 | Craig | |
| 2009/0259224 | A1 | 10/2009 | Wham | |
| 2010/0094275 | A1 | 4/2010 | Wham | |
| 2010/0217258 | A1* | 8/2010 | Floume et al. | 606/34 |
| 2010/0217264 | A1* | 8/2010 | Odom et al. | 606/48 |
| 2011/0028963 | A1* | 2/2011 | Gilbert | 606/33 |
| 2011/0054460 | A1* | 3/2011 | Gilbert | 606/33 |
| 2011/0071516 | A1* | 3/2011 | Gregg | 606/34 |
| 2011/0077631 | A1* | 3/2011 | Keller | 606/33 |
| 2011/0112530 | A1* | 5/2011 | Keller | 606/42 |
| 2011/0115562 | A1* | 5/2011 | Gilbert | 330/262 |
| 2011/0144635 | A1* | 6/2011 | Harper et al. | 606/34 |
| 2011/0208179 | A1* | 8/2011 | Prakash et al. | 606/33 |
| 2011/0213355 | A1* | 9/2011 | Behnke, II | 606/33 |

FOREIGN PATENT DOCUMENTS

| | | | |
|---|---|---|---|
| DE | 1139927 | | 11/1962 |
| DE | 1149832 | | 6/1963 |
| DE | 1439302 | | 1/1969 |
| DE | 2439587 | | 2/1975 |
| DE | 2455174 | | 5/1975 |
| DE | 2407559 | | 8/1975 |
| DE | 2602517 | | 7/1976 |
| DE | 2504280 | | 8/1976 |
| DE | 2540968 | | 3/1977 |
| DE | 2820908 | | 11/1978 |
| DE | 2803275 | | 8/1979 |
| DE | 2823291 | | 11/1979 |
| DE | 2946728 | | 5/1981 |
| DE | 3143421 | | 5/1982 |
| DE | 3045996 | | 7/1982 |
| DE | 3120102 | | 12/1982 |
| DE | 3510586 | | 10/1986 |
| DE | 3604823 | | 8/1987 |
| DE | 390937 | | 4/1989 |
| DE | 3904558 | | 8/1990 |
| DE | 3942998 | | 7/1991 |
| DE | 4206433 | | 9/1993 |
| DE | 4339049 | | 5/1995 |
| DE | 19506363 | | 8/1996 |
| DE | 19717411 | | 11/1998 |
| DE | 19848540 | | 5/2000 |
| EP | 246350 | | 11/1987 |
| EP | 267403 | | 5/1988 |
| EP | 296777 | | 12/1988 |
| EP | 310431 | | 4/1989 |
| EP | 325456 | | 7/1989 |
| EP | 336742 | | 10/1989 |
| EP | 390937 | | 10/1990 |
| EP | 556705 | | 8/1993 |
| EP | 608609 | | 8/1994 |
| EP | 836868 | | 4/1998 |
| EP | 882955 | | 12/1998 |
| EP | 1051948 | | 11/2000 |
| EP | 1053720 | A1 | 11/2000 |
| EP | 1293171 | A2 | 3/2003 |
| EP | 1500378 | A1 | 1/2005 |
| EP | 1366724 | | 1/2006 |
| EP | 880220 | | 6/2006 |
| EP | 1776929 | | 4/2007 |
| EP | 1849425 | | 10/2007 |
| EP | 1862137 | A1 | 12/2007 |
| EP | 2025297 | | 2/2009 |
| FR | 1275415 | | 10/1961 |
| FR | 1347865 | | 11/1963 |
| FR | 2313708 | | 12/1976 |
| FR | 2364461 | | 7/1978 |
| FR | 2502935 | | 10/1982 |
| FR | 2517953 | | 6/1983 |
| FR | 2573301 | | 5/1986 |
| JP | 63005876 | | 1/1988 |
| SU | 166452 | | 1/1965 |
| SU | 727201 | | 4/1980 |
| WO | WO 96/02180 | | 2/1996 |
| WO | WO 97/10763 | | 3/1997 |
| WO | WO 98/07378 | | 2/1998 |

(56) References Cited

FOREIGN PATENT DOCUMENTS

| WO | WO 98/27880 | 7/1998 |
|---|---|---|
| WO | WO02/11634 | 2/2002 |
| WO | WO02/45589 | 6/2002 |
| WO | WO03/090635 | 11/2003 |
| WO | WO 2005/046496 A1 | 5/2005 |
| WO | WO2006/050888 | 5/2006 |

OTHER PUBLICATIONS

U.S. Appl. No. 10/573,713, Mar. 2006, Robert H. Wham.*
U.S. Appl. No. 11/242,458, Oct. 2005, Daniel J. Becker.*
U.S. Appl. No. 10/406,690, filed Apr. 3, 2003.
U.S. Appl. No. 10/573,713, filed Mar. 28, 2006.
U.S. Appl. No. 10/761,524, filed Jan. 21, 2004.
U.S. Appl. No. 11/242,458, filed Oct. 3, 2005.
U.S. Appl. No. 12/351,935, filed Jan. 12, 2009.
U.S. Appl. No. 12/351,947, filed Jan. 12, 2009.
U.S. Appl. No. 12/351,960, filed Jan. 12, 2009.
U.S. Appl. No. 12/351,970, filed Jan. 12, 2009.
U.S. Appl. No. 12/351,980, filed Jan. 12, 2009.
U.S. Appl. No. 12/353,002, filed Jan. 13, 2009.
U.S. Appl. No. 12/353,012, filed Jan. 13, 2009.
U.S. Appl. No. 12/477,245, filed Jun. 3, 2009.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
U.S. Appl. No. 12/619,234, filed Nov. 16, 2009.
U.S. Appl. No. 12/639,210, filed Dec. 16, 2009.
U.S. Appl. No. 12/665,081, filed Dec. 17, 2009.
U.S. Appl. No. 12/712,712, filed Feb. 25, 2010.
U.S. Appl. No. 12/713,956, filed Feb. 26, 2010.
U.S. Appl. No. 12/715,212, filed Mar. 1, 2010.
U.S. Appl. No. 12/754,420, filed Apr. 5, 2010.
U.S. Appl. No. 12/754,429, filed Apr. 5, 2010.
U.S. Appl. No. 12/772,345, filed May 3, 2010.
Momozaki Y et al.: "Electrical breakdown experiments with application to alkalimetal thermal-to-electric converters", Energy Conversion and Management, Elsevier Science Publishers, vol. 44, #6, Apr. 1, 2003.
Zlatanovic M: "Sensors in diffusion plasma processing", Microelectronics, 1995, Proceedings, 1995, 20th Int, Conf. CE on NIS, Serbia Sep. 12-14, 1995, NY, NY, vol. 2 pp. 565-570.
European Search Report for European Application No. 11173562.7 dated Nov. 11, 2011.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.

(56) References Cited

OTHER PUBLICATIONS

International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.

* cited by examiner

POLARITY CONTROL OF ELECTROSURGICAL GENERATOR

BACKGROUND

1. Technical Field

The present disclosure relates to electrosurgical generators. More particularly, the present disclosure relates to a system and method for controlling output of an electrosurgical generator. The electrosurgical generator includes a sensing feedback control system and an electrical discharge based adaptive control system that adjusts output in response to electrical discharges.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue.

In bipolar electrosurgery, one of the electrodes of the handheld instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

Bipolar electrosurgical techniques and instruments can be used to coagulate blood vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

In monopolar electrosurgery, the active electrode is typically a part of the surgical instrument held by the surgeon that is applied to the tissue to be treated. A patient return electrode is placed remotely from the active electrode to carry the current back to the generator and safely disperse current applied by the active electrode. The return electrodes usually have a large patient contact surface area to minimize heating at that site. Heating is caused by high current densities that directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

SUMMARY

A method for controlling an electrosurgical generator is contemplated by the present disclosure. The method includes applying an electrosurgical waveform to tissue through an electrode. The electrosurgical waveform includes one or more positive half-cycles and one or more negative half-cycles. The method also includes measuring voltage and current of the waveform including peak and zero-crossing values to determine occurrence of electrical (e.g., arc and glow) discharges. The method further includes the adjusting a current of the electrosurgical waveform to regulate the generation of the electrical discharges based on a comparison of the peak voltage of the positive half-cycles and the peak voltage of the negative half-cycles.

The present disclosure also provides for an electrosurgical generator, which includes an RF output stage configured to generate at least one electrosurgical waveform including one or more positive half-cycles and one or more negative half-cycles. The generator also includes one or more sensors coupled to the RF output stage. The sensors are configured to detect instantaneous voltage and current of each of the positive half-cycles and the negative half-cycles. The generator further includes a controller coupled to the sensors. The controller may be configured to compare the peak voltage of the positive half-cycles and the peak voltage of the negative half-cycles to determine generation of electrical (e.g., arc and glow) discharges. The controller is further configured to adjust the current of the electrosurgical waveform to regulate the generation of the electrical discharges based on a comparison of the peak voltage of the positive half-cycles and the peak voltage of the negative half-cycles.

The present disclosure also provides for an electrosurgical system. The system includes an electrosurgical generator and one or more electrosurgical instruments configured to couple to the electrosurgical generator and to supply the electrosurgical waveform to the tissue. The electrosurgical generator includes an RF output stage configured to generate at least one electrosurgical waveform including one or more positive half-cycles and one or more negative half-cycles. The generator also includes one or more sensors coupled to the RF output stage. The sensors are configured to detect an instantaneous voltage of each of the positive half-cycles and the negative half-cycles. The generator further includes a controller coupled to the sensors. The controller may be configured to compare the peak voltage of the positive half-cycles and the peak voltage of the negative half-cycles to determine generation of electrical (e.g., arc and glow) discharges. The controller is further configured to adjust the current of the electrosurgical waveform to regulate the generation of the electrical discharges based on a comparison of the peak voltage of the positive half-cycles and the peak voltage of the negative half-cycles.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

During application of electrosurgical energy, electrical discharge is generated between an active electrode and the tissue. In particular, discharges are generated when an active electrode is held at a distance from the tissue. When the electrode is in direct contact with the tissue, this results in heating and subsequent desiccation of the tissue, without an electrical discharge.

Discharges can be categorized as thermal arc and glow electrical discharges. The present disclosure provides for systems and method for identifying electrical discharges and adjusting output of the electrosurgical energy to tailor generation of arc discharges or glow discharges. The type of the discharge (e.g., arc or glow) depends on a variety of factors, such as current, electrode material, electrode geometry and electrode temperature. Arc discharges occur during negative half-cycle of energy delivery, while glow discharges can occur during both, negative and positive half-cycles.

Arc and glow discharges can be identified based on the differences between the discharge characteristics of the electrosurgical energy. In particular, monitoring of the voltage and current waveforms in the positive and negative polarities allows for identification of the type of discharge. Glow discharges exhibit a higher gap voltage than arc discharge. In addition, glow discharges exhibit a higher voltage at discharge termination.

The system and method according to present disclosure detect these difference and provide for control algorithms based on the detected differences. In one embodiment, the difference between the peak voltage of the negative and positive half-cycles is utilized as a detection parameter indicative of the type of electrical discharge. In another embodiment, the system may monitor for the gap voltage value reaching zero. During procedures when the electrode is in direct contact with the tissue (e.g., desiccation), current flow continues until the gap voltage reaches zero, thus, this value is a suitable indicator of the presence of discharges. Power may be decreased or increased to either cease or initiate arc or glow discharges, respectively.

In one embodiment, the discharges may be controlled by adjusting the time between pulses to control the temperature of the active electrode. This maintains the negative half-cycle in either the arc or glow regime along with its associated surgical effects. In another embodiment, electrode temperature may be controlled by adjusting the current delivered thereto (e.g., via power adjustment).

The generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured to generate radio frequency power specifically suited for various electrosurgical modes (e.g., cutting, blending, division, etc.) and procedures (e.g., monopolar, bipolar, vessel sealing).

Figure 1:
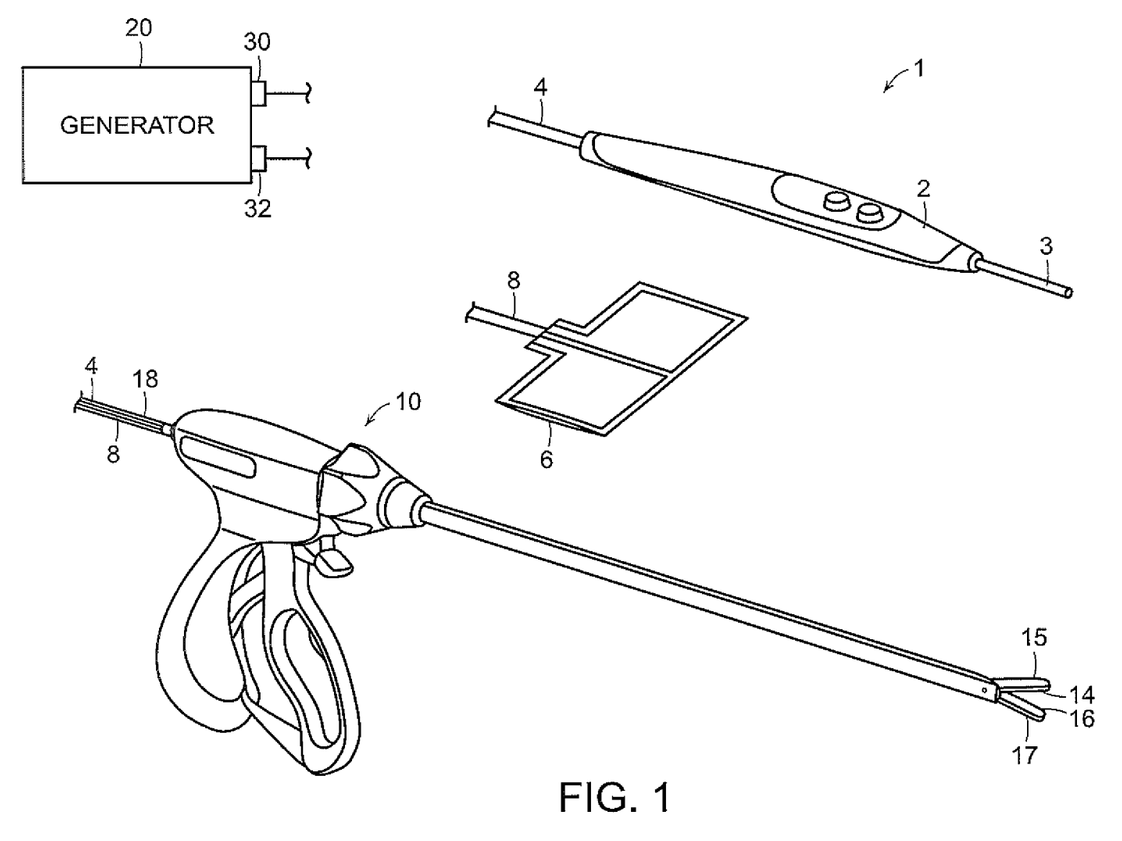
FIG. 1 is a schematic diagram of an electrosurgical system according to one embodiment of the present disclosure.

FIG. 1 is a schematic illustration of a bipolar and monopolar electrosurgical system 1 according to one embodiment of the present disclosure. The system 1 includes one or more monopolar electrosurgical instruments 2 having one or more electrodes 3 (e.g., electrosurgical cutting probe, ablation electrode(s), etc.) for treating tissue of a patient. Electrosurgical RF energy is supplied to the instrument 2 by a generator 20. The instrument 2 includes an active electrode 3 that is connected via a supply line 4 to an active terminal 30 of the generator 20, allowing the instrument 2 to coagulate, ablate and/or otherwise treat tissue. The energy is returned to the generator 20 through a return electrode 6 via a return line 8 at a return terminal 32 of the generator 20. The system 1 may include a plurality of return electrodes 6 that are arranged to minimize the chances of tissue damage by maximizing the overall contact area with the patient. In addition, the generator 20 and the return electrode 6 may be configured for monitoring so-called "tissue-to-patient" contact to insure that sufficient contact exists therebetween to further minimize chances of tissue damage.

The system 1 may also include a bipolar electrosurgical forceps 10 having one or more electrodes for treating tissue of a patient. The electrosurgical forceps 10 includes opposing jaw members 15 and 17 having one or more active electrodes 14 and a return electrode 16 disposed therein, respectively. The active electrode 14 and the return electrode 16 are connected to the generator 20 through cable 18 that includes the supply and return lines 4, 8 coupled to the active and return terminals 30, 32, respectively. The electrosurgical forceps 10 is coupled to the generator 20 at a connector having connections to the active and return terminals 30 and 32 (e.g., pins) via a plug disposed at the end of the cable 18, wherein the plug includes contacts from the supply and return lines 4, 8.

Figure 2:
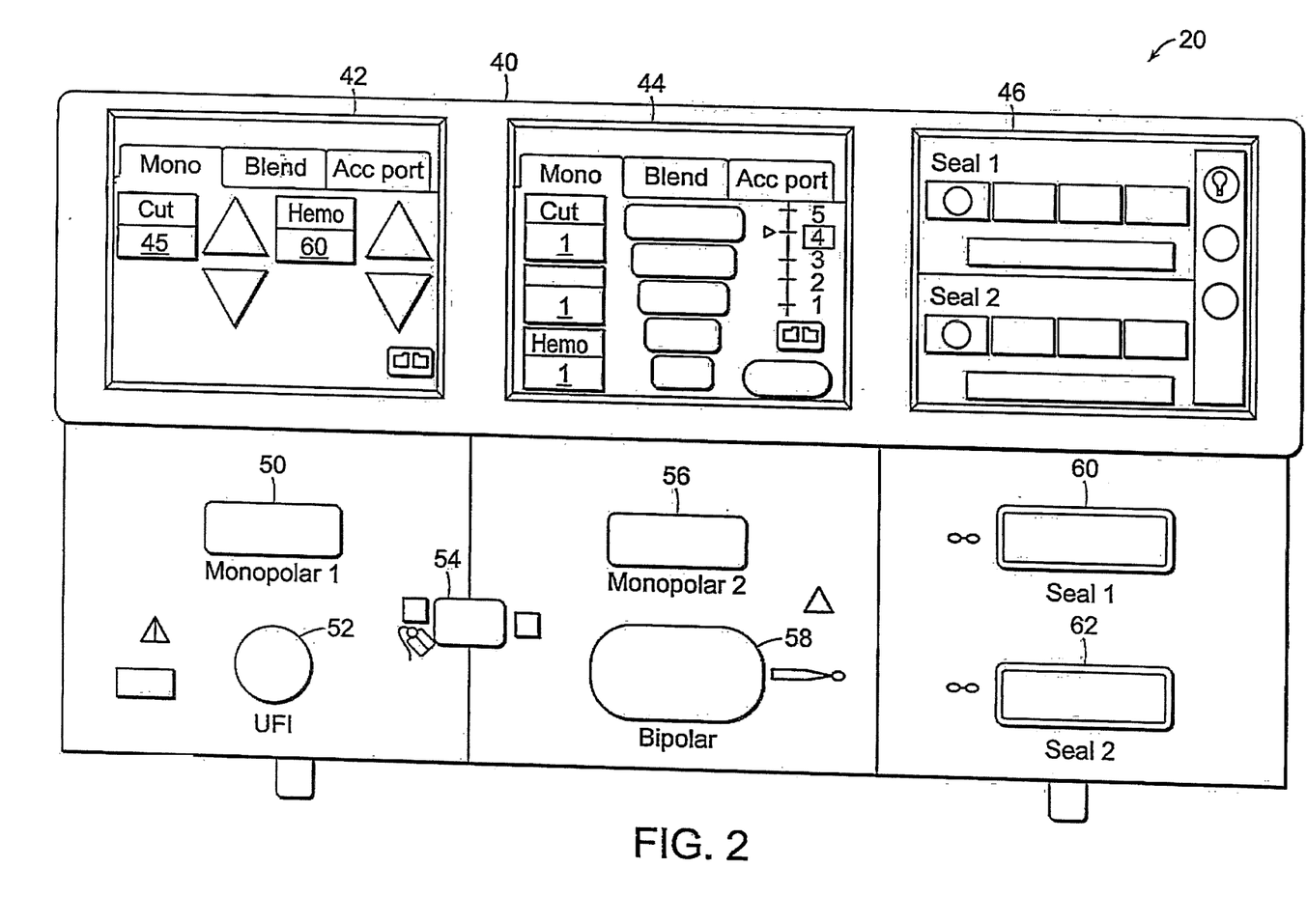
FIG. 2 is a front view of an electrosurgical generator according to an embodiment of the present disclosure.

With reference to FIG. 2, front face 40 of the generator 20 is shown. The generator 20 may be any suitable type (e.g., electrosurgical, microwave, etc.) and may include a plurality of connectors 50-62 to accommodate various types of electrosurgical instruments (e.g., multiple instruments 2, electrosurgical forceps 10, etc.). The generator 20 includes one or more display screens 42, 44, 46 for providing the user with a variety of output information (e.g., intensity settings, treatment complete indicators, etc.). Each of the screens 42, 44, 46 is associated with a corresponding connector 50-62. The generator 20 includes suitable input controls (e.g., buttons, activators, switches, touch screen, etc.) for controlling the generator 20. The display screens 42, 44, 46 are also configured as touch screens that display a corresponding menu for the electrosurgical instruments (e.g., multiple instruments 2, electrosurgical forceps 10, etc.). The user then makes inputs by simply touching corresponding menu options. The controls allow the user to select desired output modes as well as adjust operating parameters of the modes, such as power, waveform parameters, etc. to achieve the desired output suitable for a particular task (e.g., cutting, coagulating, tissue sealing, etc.).

The generator 20 is configured to operate in a variety of modes. In one embodiment, the generator 20 may output the following modes, cut, blend, division with hemostasis, fulgurate and spray. Each of the modes operates based on a preprogrammed power curve that dictates how much power is outputted by the generator 20 at varying impedance ranges of the load (e.g., tissue). Each of the power curves includes a constant power, constant voltage and constant current ranges that are defined by the user-selected power setting and the measured minimum impedance of the load.

In the cut mode, the generator 20 supplies a continuous sine wave at a predetermined frequency (e.g., 472 kHz) having a crest factor of 1.5 or less in the impedance range of 100Ω to 2,000Ω. The cut mode power curve may include three regions: constant current into low impedance, constant power into medium impedance and constant voltage into high impedance. In the blend mode, the generator supplies bursts of a sine wave at the predetermined frequency, with the bursts reoccurring at a first predetermined rate (e.g., about 26.21 kHz). In one embodiment, the duty cycle of the bursts may be about 50%. The crest factor of one period of the sine wave may be less than 1.5. The crest factor of the burst may be about 2.7.

The division with hemostasis mode includes bursts of sine waves at a predetermined frequency (e.g., 472 kHz) reoccurring at a second predetermined rate (e.g., about 28.3 kHz). The duty cycle of the bursts may be 25%. The crest factor of one burst may be 4.3 across an impedance range of 100Ω to 2,000Ω. The fulgurate mode includes bursts of sine waves at a predetermined frequency (e.g., 472 kHz) reoccurring at a third predetermined rate (e.g., about 30.66 kHz). The duty cycle of the bursts may be 6.5% and the crest factor of one burst may be 5.55 across an impedance range of 100Ω to 2,000Ω. The spray mode may be bursts of sine wave at a predetermined frequency (e.g., 472 kHz) reoccurring at a third predetermined rate (e.g., about 21.7 kHz). The duty cycle of the bursts may be 4.6% and the crest factor of one burst may be 6.6 across the impedance range of 100Ω to 2,000 Ω.

The screen 46 controls bipolar sealing procedures performed by the forceps 10 that may be plugged into the connectors 60 and 62. The generator 20 outputs energy through the connectors 60 and 62 suitable for sealing tissue grasped by the forceps 10. The screen 42 controls monopolar output and the devices connected to the connectors 50 and 52. The connector 50 is configured to couple to the instrument 2 and the connector 52 is configured to couple to a foot switch (not shown). The foot switch provides for additional inputs (e.g., replicating inputs of the generator 20 and/or instrument 2). The screen 44 controls monopolar and bipolar output and the devices connected to the connectors 56 and 58. Connector 56 is configured to couple to the instrument 2, allowing the generator 20 to power multiple instruments 2. Connector 58 is configured to couple to a bipolar instrument (not shown). When using the generator 20 in monopolar mode (e.g., with instruments 2), the return electrode 6 is coupled to the connector 54, which is associated with the screens 42 and 44. The generator 20 is configured to output the modes discussed above through the connectors 50, 56, 58.

Figure 3:
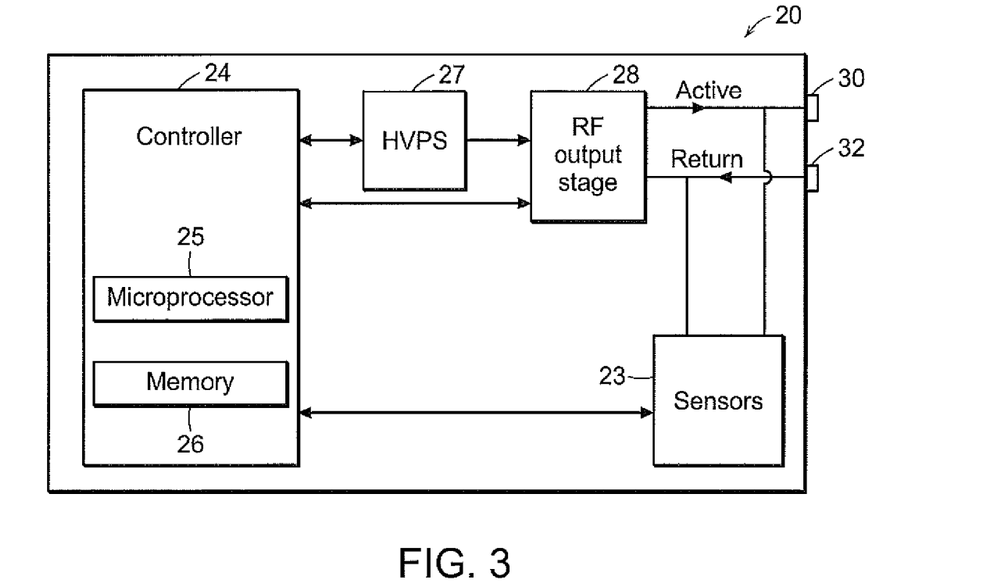
FIG. 3 is a schematic block diagram of the electrosurgical generator of FIG. 2 according to an embodiment of the present disclosure.

FIG. 3 shows a schematic block diagram of the generator 20 having a controller 24, a high voltage DC power supply 27 ("HVPS") and an RF output stage 28. The HVPS 27 is connected to an AC source (e.g., electrical wall outlet) and provides high voltage DC power to an RF output stage 28, which then converts high voltage DC power into RF energy and delivers the RF energy to the active terminal 30. The energy is returned thereto via the return terminal 32. In particular, the RF output stage 28 generates sinusoidal waveforms of high RF energy. The RF output stage 28 is configured to operate in a plurality of modes, during which the generator 20 outputs corresponding waveforms having specific duty cycles, peak voltages, crest factors, etc. In another embodiment, the generator 20 may be based on other types of suitable power supply topologies.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RE output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop, in which one or more sensors 23 measure a variety of tissue and/or energy properties (e.g., tissue impedance, tissue temperature, output current and/or voltage, etc.), and provide feedback to the controller 24, Such sensors may include voltage and current sensors that are coupled to the output terminals 30 and 32 of the generator 20, which are within the purview of those skilled in the art. In response to the sensor signals, the controller 24 controls the HVPS 27 and/or RF output stage 28, which then adjusts the DC and/or RF power supply, respectively. The controller 24 also receives input signals from the input controls of the generator 20, the instrument 2 or forceps 10. The controller 24 utilizes the input signals to adjust power outputted by the generator 20 and/or performs other control functions thereon.

Figure 4:
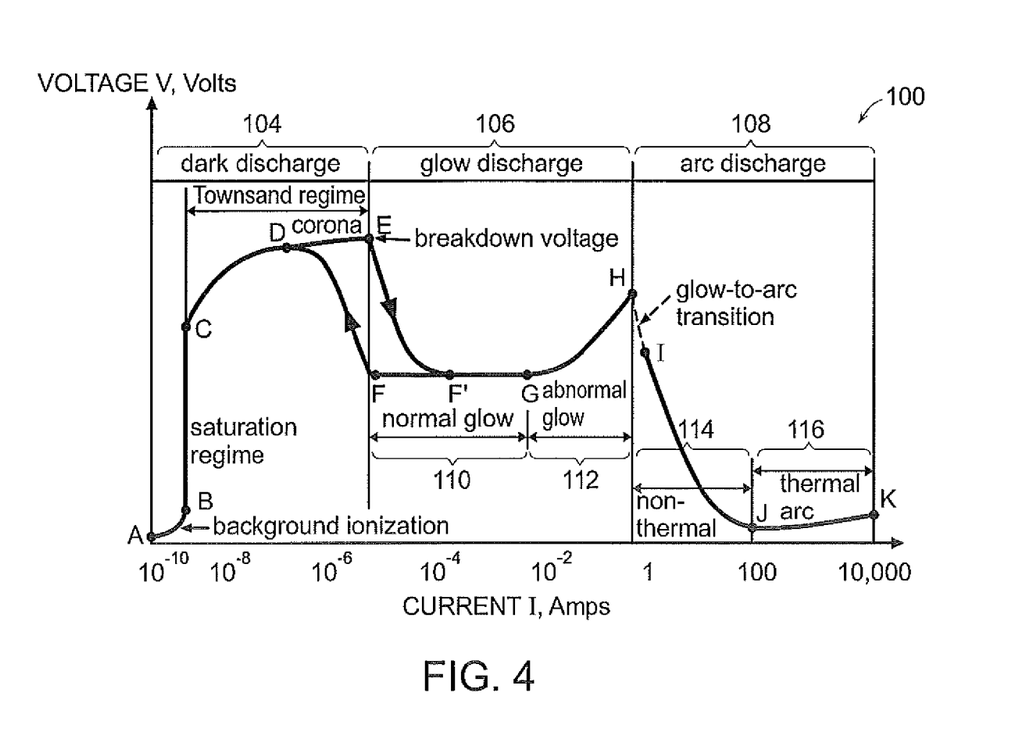
FIG. 4 is a plot of a voltage and current illustrating electrical discharges according to an embodiment of the present disclosure.

FIG. 4 shows a plot 100 of voltage versus current illustrating generation of possible discharges during application of electrosurgical energy to an electrode (e.g., electrode 3) that is spaced a predetermined distance apart from the tissue. The plot 100 includes three discharge regions a dark discharge region 104, a glow discharge region 106 and an arc discharge 108. During the dark discharge region 104, electrical energy is supplied to the active electrode 3 at high voltage but low current. At point A background ionization occurs at the electrode 3 in response to the electrical energy supplied thereto. Between points B and C, saturation regime is taking place as voltage is increasing while current stays relatively constant. Voltage continues to increase through the points C and D, during which electrons start escaping from the electrode 3. The electrons are transmitted through the air onto the tissue. Interaction of the electrons with the gas molecules results in a formation of a corona between the points D and E as voltage increase slows down, which is characterized by the Townsend effect.

The glow discharge regime 106 occurs after the breakdown voltage of the air is reached (e.g., at points D and/or E). The glow discharge regime 106 includes a normal glow discharge 110 between points F and G and an abnormal glow discharge 112 between the points G and H. During the normal glow discharge 110, the voltage remains constant while the current continues to increase. During the abnormal glow discharge 112, the voltage and current are increasing almost in a linear manner until the arc discharge regime 108 is reached.

During the arc discharge regime 108, the voltage decreases precipitously between points I and J, producing a non-thermal discharge 114. The voltage stabilizes between the points J and K, producing the a thermal arc 116. The arc discharge regime 108 the current is increasing continuously. As stated above, arc discharges (e.g., arc discharge regime 108) occur on the negative half-cycles, whereas glow discharges (e.g., glow discharge regime 106) can occur on either half-cycles depending on the temperature of the electrode 3. One of the characteristics of the thermal arc 116 is a relatively low voltage as illustrated by the plot 100.

Figure 5:
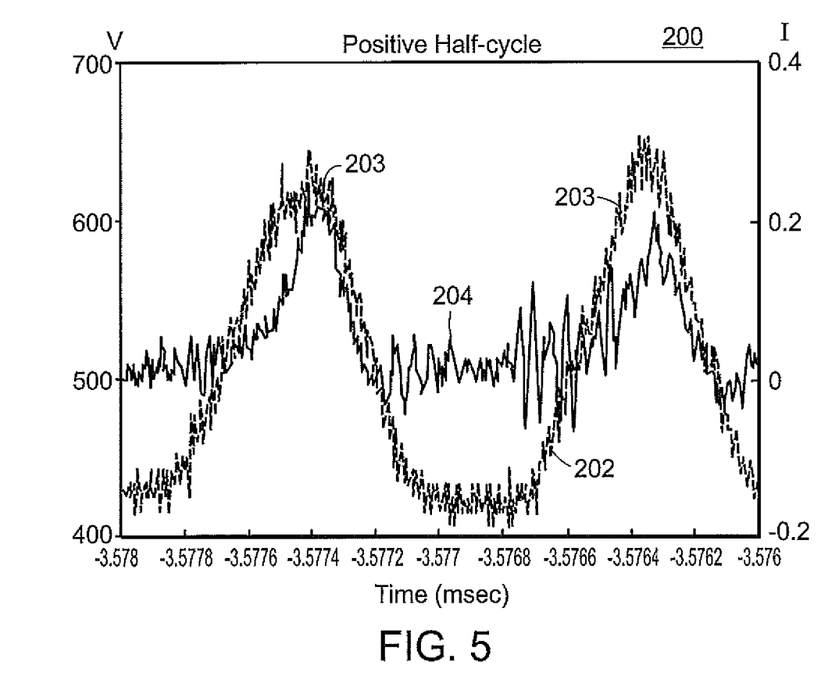
FIG. 5 is a plot of voltage and current waveforms illustrating differences between electrical discharges according to an embodiment of the present disclosure.
Figure 6:
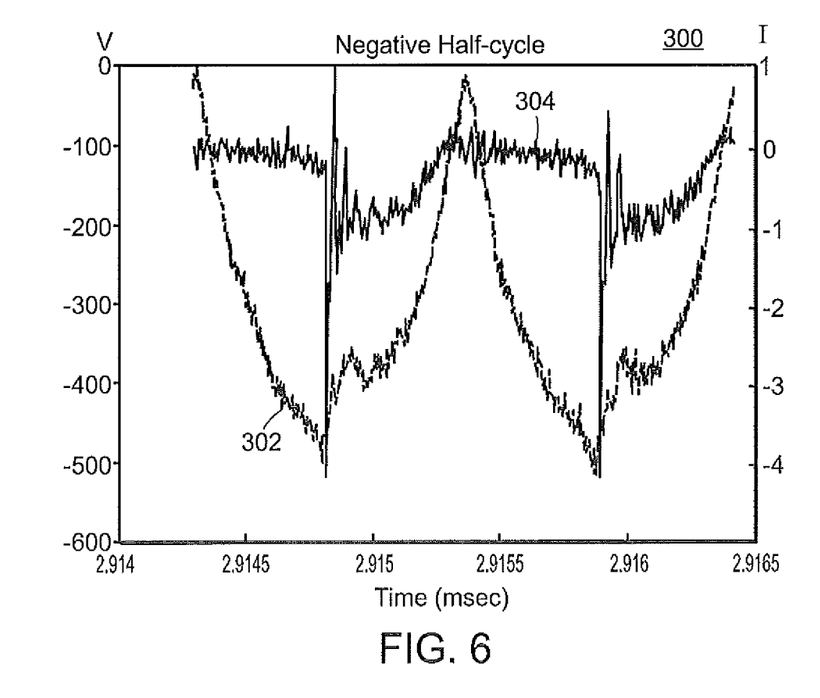
FIG. 6 is a plot of voltage and current waveforms illustrating differences between electrical discharges according to an embodiment of the present disclosure.
Figure 7:
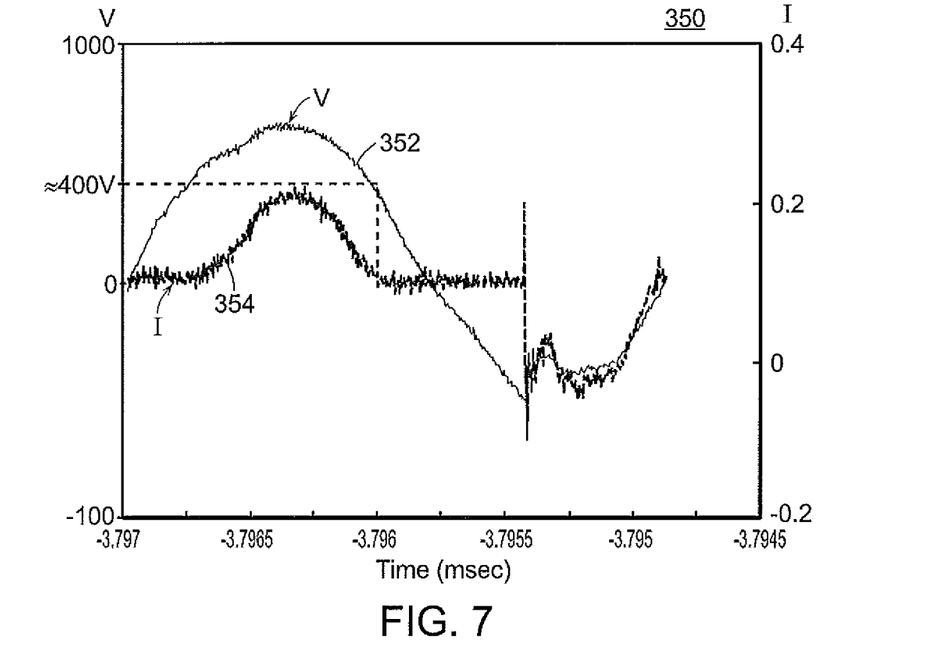
FIG. 7 is a plot of voltage and current waveforms illustrating differences between electrical discharges according to an embodiment of the present disclosure.

FIGS. 5, 6 and 7 illustrate plots 200, 300, and 350, respectively, of voltage and current of arc and glow discharges. FIG.

5 illustrates a rectified positive half-cycle plot 200 and FIG. 6 illustrates a rectified negative half-cycle plot 300 of a positive rectified 50 W cut signal. FIG. 7 illustrates an unrectified complete cycle plot 350 of 50 W cut signal. The plot 200 includes a positively-rectified, symmetrical, sinusoidal voltage waveform 202 having two positive half-cycles 203 and a current waveform 204. The plot 300 includes a negatively-rectified, symmetrical, sinusoidal voltage waveform 302 having two negative half-cycles 303 and a current waveform 304. The plot 350 includes a voltage waveform 352 and a current waveform 354.

The plots 200 and 300 illustrate that the arc discharge can be predicted to occur during the negative half-cycle, specifically, when the peak voltage of negative half-cycle 303 is less than the peak voltage positive half-cycle 203. The arc discharge is characterized by the current going negative and increasing in amplitude during the negative half-cycle 303 of the current waveform 304. The peak voltage of the positive half-cycle 203 is above 600 V, whereas the peak voltage of the negative half-cycle 303 is only about −500 V at the same power setting and arcing condition (e.g., electrode-to-tissue distance, tissue volume, etc.).

With respect to FIG. 6, the voltage waveform 302 illustrates another difference between arc and glow discharges, namely, the termination voltage for the discharges. In a glow discharge, current stops flowing at a higher voltage than the voltage of an arc discharge. The positive rectified current that is associated with the glow discharge stops flowing at approximately −500 V, as shown in plot 200, whereas the negative rectified current that is associated with the arc discharge stops flowing at approximately −100 V, as shown in plot 300.

The plot 350 illustrates that the arc discharge may also be predicted to occur when the current waveform 354 reaches zero crossing, namely, 0 A before the zero-crossing of the voltage waveform 352, e.g., reaches 0 V during either positive or negative half-cycles. In particular, zero-crossing of the current waveform 354 prior to zero-crossing of the voltage waveform 352 during a positive half-cycle is indicative of a glow discharge, whereas zero-crossing of the current waveform 354 prior to zero-crossing of the voltage waveform 352 during a negative half-cycle is indicative of an arc discharge. As shown in FIG. 7, during the positive half-cycle, the current waveform 354 reaches 0 A about 0.25 μs prior to the voltage waveform reaching 0 V. More specifically, during the negative half-cycle, at the time of the zero-crossing of the current waveform 354, the voltage is about +400 V. During the negative half-cycle, the current waveform reaches 0 A about 0.05 μs prior to the voltage waveform reaching 0 V, while during the positive half-cycle, at the time of the zero-crossing of the current waveform 354, the voltage is about −50 V.

Figure 8:
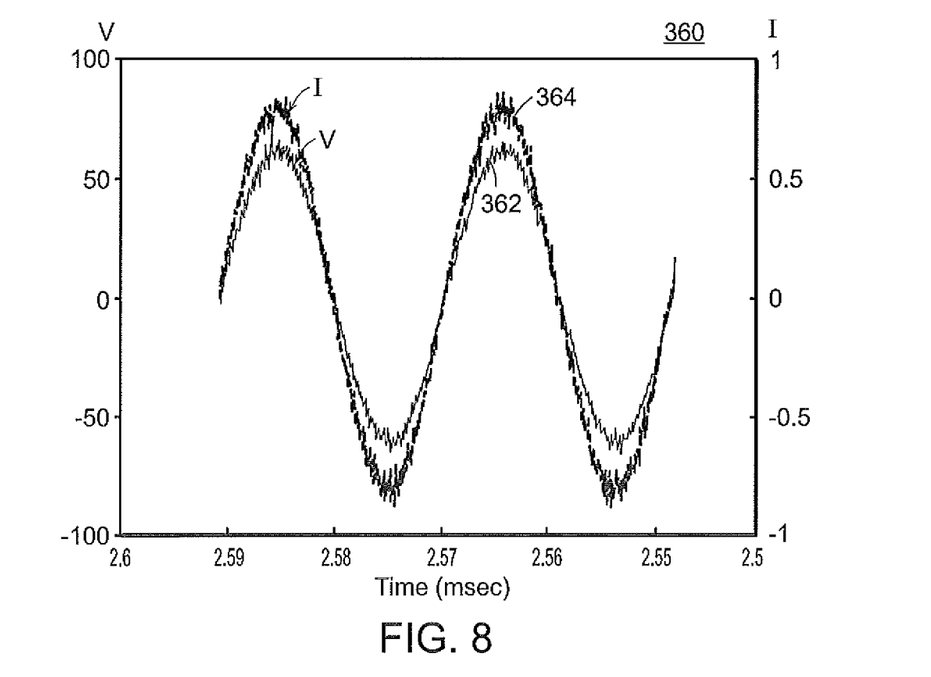
FIG. 8 is a plot of voltage and current waveforms illustrating simultaneous zero-crossing according to an embodiment of the present disclosure.

If the electrode 3 comes in direct contact with the tissue (e.g., electrode 3 being in resistive contact without arcing forming through the air gap), the voltage and current reach 0 V and 0 A simultaneously. This condition may be utilized to distinguish between an arc-forming configuration (e.g., electrode 3 being held away from the tissue) and a contact configuration that is suitable for desiccating tissue (e.g., electrode 3 being in direct contact with the tissue). FIG. 8 illustrates the plot 360 of the voltage waveform 362 and the current waveform 364 in a resistive manner due to direct electrode-to-tissue contact. Each of the voltage waveform 362 and the current waveform 364 are zero-crossing concurrently, indicative of direct contact.

Plot 300 also illustrates that when the voltage waveform 302 is of symmetrical shape, the arc and glow discharges exhibit different resistances. In the present example, the positive half-cycle 203a has a resistance of approximately 3,000Ω, whereas the negative half-cycle 203b has a resistance of approximately 275 Ω.

Based on the illustrated plot 200, it follows that output voltage may be utilized to determine whether the electrode 3 is in contact with the tissue and no discharges are going to produced or the electrode 3 is disposed a predetermined distance apart from the tissue and discharges may be generated. The current waveform reaching 0 A prior to the voltage waveform reaching 0 V is also indicative of electrical discharges. More specifically, zero-crossing of the current-waveform prior to that of the voltage waveform during the positive half-cycle is indicative of a glow discharge, whereas zero-crossing of the current-waveform prior to that of the voltage waveform during the negative half-cycle is indicative of an arc discharge. Output voltage may also be used to distinguish between the types of discharges. Namely, if the peak voltage of negative half-cycle 303 is less than the peak voltage positive half-cycle 203, then it may be predicted that the arc discharge is produced during the negative half-cycle 303.

Another factor that affects the formation of the arc discharges is the temperature of the electrode. Due to thermionic emission, an increased temperature of the electrode 3 results in higher incidence of arc discharges, whereas a lower temperature of the electrode 3 impedes formation of the arc discharges. In particular, higher temperature result in higher electron emission, which directly contribute to the generation of various discharges.

The relationship between output voltage at positive and negative half-cycles 203 and 303, makes it possible for the generator 20 to adjust its output in response to the detected arc discharges. Since arc discharges (e.g., thermal and non-thermal arcs) occur during a negative half-cycle of the voltage waveform due to the heating of the electrode 3, upon detecting arc discharges, the generator 20 may increase the time between pulses (e.g., lower the duty cycle) to allow the electrode 3 to cool and remain in the glow discharge regime 106. In another embodiment, the generator 20 may reduce the current to prevent the electrode 3 from overheating. Conversely, shortening the time between pulses may be used to insure that the negative half-cycles remain in the arc discharge regime 108, when arc discharges are desired (e.g., cutting). The adjustments to the generator 20 may be embodied in either hardware and/or software to be performed automatically or in response to user input (e.g., entering pulse delay). In a further embodiment, the generator 20 is configured to detect a resistive contact between the electrode 3 and the tissue (e.g., 0 V simultaneous with 0 A) and increase power and/or voltage to initiate arc discharges or lower power or voltage to extinguish arc discharges.

Figure 9:
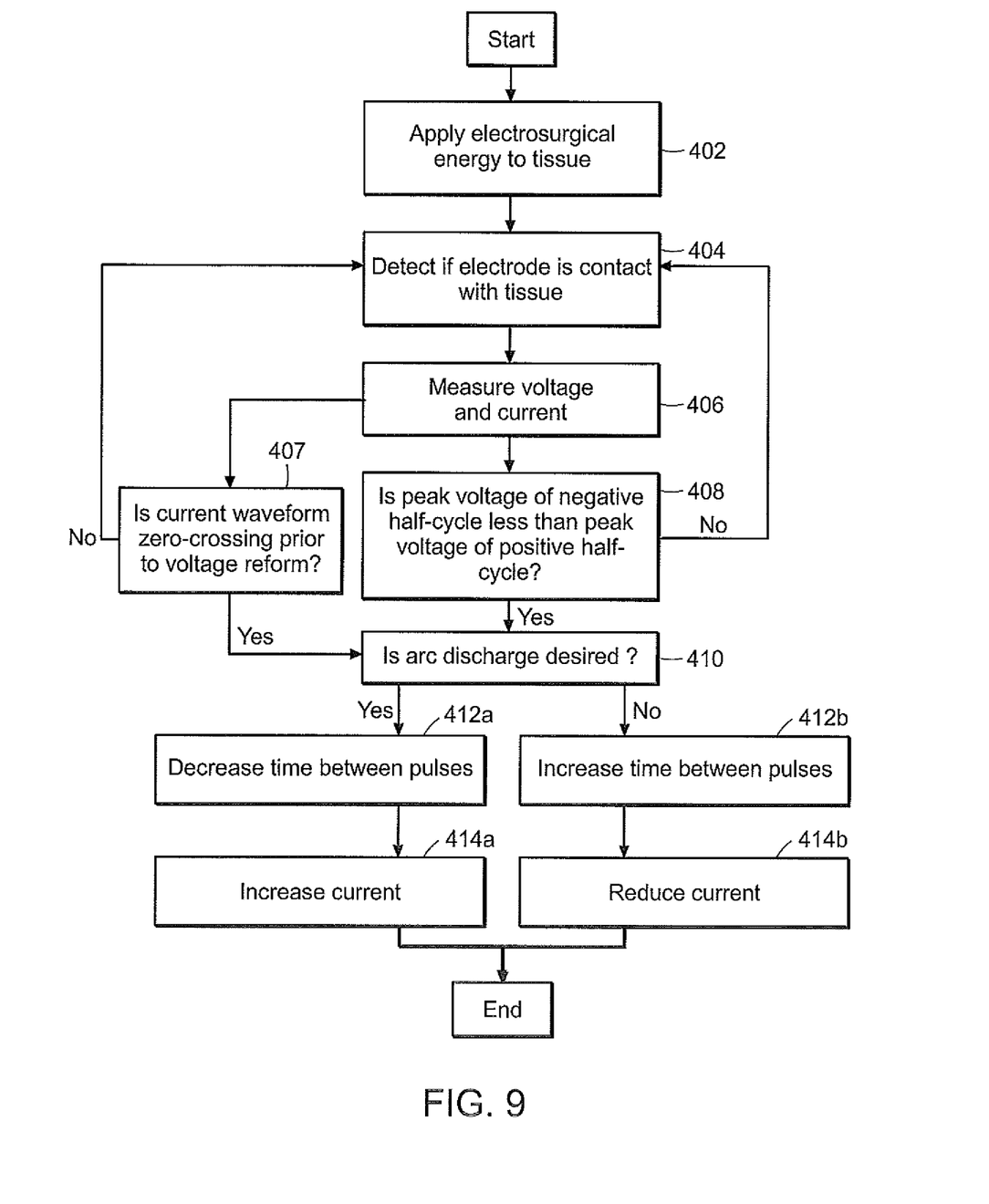
FIG. 9 is a flow chart of a method according to an embodiment of the present disclosure.

FIG. 9 illustrates a method for detecting arc discharges and adjusting the occurrence thereof. In step 402, electrosurgical energy is applied to tissue through the instrument 2 in one of the modes outlined above. In step 404, the generator 20 determines whether the electrode 3 is in contact with the tissue. In particular, the sensors 23 monitor voltage until the voltage reaches 0 V simultaneous with 0 A. This measurement is indicative of a contact condition, when the electrode 3 is in resistive contact with the tissue, without producing any arc discharges.

If the electrode 3 is not in contact with the tissue, e.g., when the voltage is at a non-zero value, arc discharges are possible. The generator 20 detects such arc discharges in steps 406, 407 and 408.

In step 406, the sensors 23 measure voltage and current including peak voltage for each of the positive and negative half-cycles as well as zero-crossing of the voltage and current waveforms. In step 407, the measurements are transmitted to the controller 24, which determines whether the zero-crossing of the current-waveform prior to that of the voltage waveform during the positive half-cycle and the negative half-cycle, which is indicative of occurrence of glow and arc discharges, respectively. In step 408, the controller 24 compares the peak voltages of the positive and negative half-cycles. If the peak voltage of the negative half-cycle is less than the peak voltage of the positive half-cycle, which is indicative of occurrence the arc discharges.

If arc or glow discharges are occurring as determined in steps 407 and 408, then the method proceed to step 410. If the peak voltage of the negative half-cycle is not larger than that of the positive half-cycle and the voltage is greater than 0 while the current is about 0 A and/or the current waveform is not zero-crossing prior to that of the voltage waveform, then the method continues to monitor for electrode-to-tissue contact and measuring the peak voltage in steps 404 and 406.

In step 410, the controller 24 determines whether the arc discharges are desired based on manual (e.g., user input) or automatic input. In one embodiment, the user may specifically toggle an option for generating arc discharges. In another embodiment, the arc discharges may be toggled based on the selected mode (e.g., if cut mode is selected, arc discharges are to be maximized). If arc discharges are desired, in step 412a the controller 24 decreases the time between pulses of the electrosurgical waveform, this is applicable in situations where the duty cycle is from about 1% to about 99%, in embodiments from about 10% to about 80%. In addition, the controller 24 also increases the current in step 414a, which, in turn, increases the temperature of the electrode 3. Both of these factors contribute to generation of arc discharges for the reasons outlined above. The steps 412b and 414b have an opposite effect on arc discharge generation than the steps 412a and 414a. If arc discharge generation is undesired, then in step 412b the controller 24 increases the time between pulses and reduces the current in step 414b to reduce the temperature.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for controlling an electrosurgical generator, the method comprising:
applying at least one electrosurgical waveform to tissue through at least one electrode, the at least one electrosurgical waveform including a plurality of cycles, each cycle having one positive half-cycle and one negative half-cycle;
measuring a voltage and a current of the at least one electrosurgical waveform to determine a peak voltage of each of the positive half-cycle and the negative half-cycle;
comparing the peak voltage of the positive half-cycle and the peak voltage of the negative half-cycle to determine generation of electrical discharges; and
adjusting the current of the at least one electrosurgical waveform to regulate the generation of the electrical discharges during each of the cycles based on a comparison of the peak voltage of the positive half-cycle and the peak voltage of the negative half-cycle.

2. The method according to claim 1, wherein the comparing further includes determining whether the peak voltage of the negative half-cycle is less than the peak voltage of the positive half-cycle.

3. The method according to claim 1, further comprising determining whether the voltage and the current of the at least one electrosurgical waveform reach a zero value simultaneously to determine whether the at least one electrode is in contact with the tissue.

4. The method according to claim 1, wherein the adjusting further includes increasing the current of the at least one electrosurgical waveform to increase the generation of the electrical discharges.

5. The method according to claim 1, wherein the adjusting further includes decreasing the current of the at least one electrosurgical waveform to decrease the generation of the electrical discharges.

6. The method according to claim 1, wherein the at least one electrosurgical waveform includes a duty cycle of less than 100% but greater than 0%.

7. The method according to claim 6, further comprising increasing the duty cycle of the at least one electrosurgical waveform to increase the generation of the electrical discharges.

8. The method according to claim 6, further comprising decreasing the duty cycle of the at least one electrosurgical waveform to decrease the generation of the electrical discharges.

9. An electrosurgical generator, comprising:
an RF output stage configured to generate at least one electrosurgical waveform including a plurality of cycles, each cycle having one positive half-cycle and one negative half-cycle;
at least one sensor coupled to the RF output stage, the at least one sensor configured to measure a voltage and a current of the at least one electrosurgical waveform and to detect a peak voltage of each of the positive half-cycle and the negative half-cycle; and
a controller coupled to the at least one sensor, the controller configured to compare the peak voltage of the positive half-cycle and the peak voltage of the negative half-cycle to determine generation of electrical discharges, the controller further configured to adjust the current of the at least one electrosurgical waveform to regulate the generation of the electrical discharges during each of the cycles based on a comparison of the peak voltage of the positive half-cycle and the peak voltage of the negative half-cycle.

10. The electrosurgical generator according to claim 9, wherein the controller is further configured to determine whether the peak voltage of the negative half-cycle is less than the peak voltage of the positive half-cycle.

11. The electrosurgical generator according to claim 9, wherein the controller is further configured to increase the current of the at least one electrosurgical waveform to increase the generation of the electrical discharges.

12. The electrosurgical generator according to claim 9, wherein the controller is further configured to decrease the current of the at least one electrosurgical waveform to decrease the generation of the electrical discharges.

13. The electrosurgical generator according to claim 9, wherein the at least one electrosurgical waveform includes a duty cycle of less than 100% but greater than 0%.

14. The electrosurgical generator according to claim 13, wherein the controller is further configured to increase the duty cycle of the at least one electrosurgical waveform to increase the generation of the electrical discharges.

15. The electrosurgical generator according to claim 13, wherein the controller is further configured to decrease the duty cycle of the at least one electrosurgical waveform to decrease the generation of the electrical discharges.

16. An electrosurgical system, comprising:
an electrosurgical generator including:
- an RF output stage configured to generate at least one electrosurgical waveform including a plurality of cycles, each cycle having one positive half-cycle and one negative half-cycle;
- at least one sensor coupled to the RF output stage, the at least one sensor configured to measure a voltage and a current of the at least one electrosurgical waveform and to detect a peak voltage of each of the positive half-cycle and the negative half-cycle; and
- a controller coupled to the at least one sensor, the controller configured to compare the peak voltage of the positive half-cycle and the peak voltage of the negative half-cycle to determine generation of electrical discharges, the controller further configured to adjust the current of the at least one electrosurgical waveform to regulate the generation of the electrical discharges during each of the cycles based on a comparison of the peak voltage of the positive half-cycle and the peak voltage of the negative half-cycle; and
at least one electrosurgical instrument configured to couple to the electrosurgical generator and to supply the at least one electrosurgical waveform to a tissue.

17. The electrosurgical system according to claim 16, wherein the controller is configured to determine whether the voltage and the current of the at least one electrosurgical waveform reach a zero value simultaneously to determine whether the at least one electrode is in contact with the tissue.

18. The electrosurgical system according to claim 16, wherein the controller is further configured to determine whether the peak voltage of the negative half-cycle is less than the peak voltage of the positive half-cycle.

19. The electrosurgical system according to claim 16, wherein the controller is further configured to increase the current of the at least one electrosurgical waveform to increase the generation of the electrical discharges.

20. The electrosurgical system according to claim 16, wherein the controller is further configured to decrease the current of the at least one electrosurgical waveform to decrease the generation of the electrical discharges.

* * * * *